United States Patent [19]

Szántay et al.

[11] Patent Number: 4,659,816

[45] Date of Patent: Apr. 21, 1987

[54] PROCESS FOR THE PREPARATION OF DIMERIC ALKALOIDS

[75] Inventors: Csaba Szántay; Katalin Honty; Lajos Szabó; Tibor Keve; Tibor Ács, all of Budapest, Hungary

[73] Assignee: Richter Gedeon Vegyeszeti Gyar R.T., Budapest, Hungary

[21] Appl. No.: 688,932

[22] Filed: Jan. 4, 1985

[30] Foreign Application Priority Data

Jan. 6, 1984 [HU] Hungary .................................. 49/84

[51] Int. Cl.$^4$ .......................................... C07D 519/04
[52] U.S. Cl. ...................................... 540/478; 546/51
[58] Field of Search ...................... 546/51; 260/244.4; 540/478

[56] References Cited

U.S. PATENT DOCUMENTS 3,481,937 12/1969 Renner et al. ................ 260/244.4 X
3,899,493 8/1975 Jovanovics et al. .............. 260/244.4
4,303,584 12/1981 Pearce ............................ 260/244.4
4,375,432 3/1983 Conrad ............................ 260/244.4

OTHER PUBLICATIONS

Ziegler, et al., J. Am. Chem. Soc., vol. 95, No. 22, pp. 7458–7464 (1973).
Langlois, et al., Helv. Chim. Acta, vol. 63, No. 4, pp. 793–805 (1980).
Döe de Maindreville, et al., Bull. Soc. Chim. France, 1981, (5–6, Pt. 2), pp. 179–184 (1981).

Primary Examiner—Robert Gerstl
Assistant Examiner—Diana G. Rivers
Attorney, Agent, or Firm—Karl F. Ross; Herbert Dubno

[57] ABSTRACT

A process is disclosed for the preparation of dimeric alkaloids of formula (II)

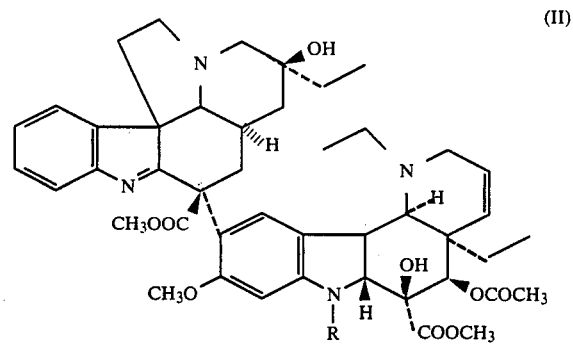

wherein R stands for methyl or formyl, as well as acid addition salts thereof which comprises oxidizing the vinblastine of formula (III)

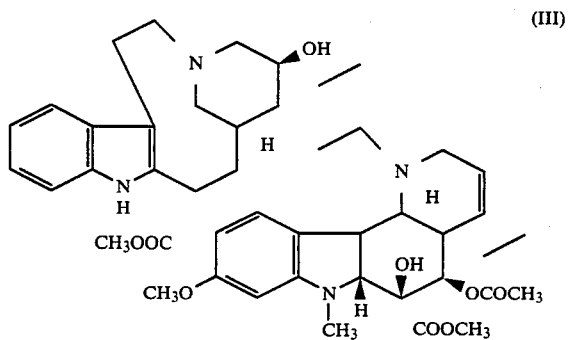

with chromium (VI) oxide or bichromate or chromic acid alcohol ester in an inert solvent, converting the compound of formula (II), wherein R stands for methyl, so obtained to the acid addition salt and optionally further oxidizing the acid addition salt obtained with an oxidizing agent as defined above and optionally converting the compound of formula (II), wherein R stands for formyl, so obtained to the acid addition salt.

3 Claims, No Drawings

PROCESS FOR THE PREPARATION OF DIMERIC ALKALOIDS

The invention relates to the preparation of new dimeric alkaloids of formula (II)

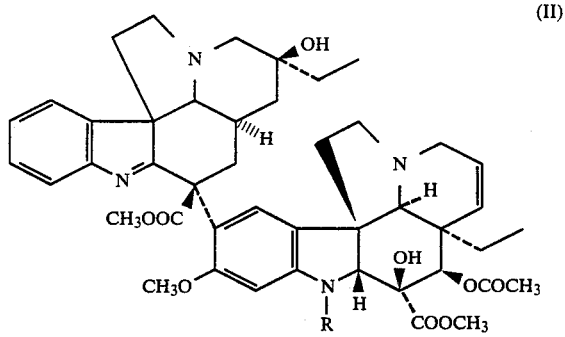

wherein R stands for methyl or formyl, as well as the acid addition salts thereof.

The invention also relates to the preparation of vincristine of formula (I)

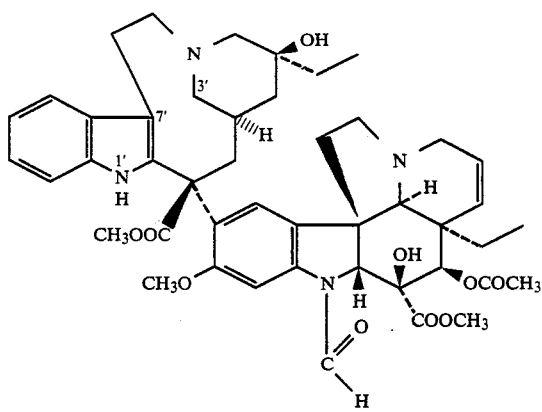

from the new compounds of formula (II).

The vincristine of formula (I) is a known compound which has cytostatic activity. This compound may be obtained from the plant Vinca rosea by extraction e.g. according to U.S. Pat. No. 3,205,220 and Hungarian Patent Specification No. 160,967 (corresponding to Belgian Patent Specification No. 773,265). Vincristine may be prepared also in a semisynthetic manner, by formylation of N-desmethyl-vinblastine (Hungarian Patent Specification No. 164,958, corresponding to Belgian Patent Specification No. 793,336) or by oxidation of vinblastine or the acid addition salt thereof (Hungarian Patent Specification No. 165,599, corresponding to U.S. Pat. No. 3,889,493 or European Patent Specification No. 79,785).

While studying the oxidation reactions of vinblastine or the acid addition salt thereof it has been found that various reaction products are obtained depending thereon whether the starting material is present as a base or as an acid addition salt, or protic or aprotic solvent is used as oxidation medium, or on the proton (acid) concentration of the solvent mixture applied. When the acid addition salt is applied as starting material the use of proton (acid) or aprotic solvent promotes the formation of vincristine. When vinblastine is oxidized in form of the free base in the absence of protons in an aprotic solvent, then a compound cyclized in the 3',7'-position transannular (new compound of formula (II), wherein R stands for methyl, further on named as cyclovinblastine) is obtained. This compound may be converted to the acid addition salt and this may be oxidized further and so the new compound containing a formyl group in place of R (further on named as cyclovincristine) is obtained. The compound so obtained possess in vitro cytostatic activity in HeLa cell culture.

Since the product of the oxidation of vinblastine depends on many factors, vincristine may be obtained together with cyclovincristine. In this case, which occurs rarely, the cyclovincristine impurity may be eliminated by converting cyclovincristine to vincristine. This may be performed preferably by reduction of cyclovincristine to vincristine using an alkali metal borohydride.

Thus according to one feature of the present invention there is provided a process for the preparation of dimeric alkaloids of formula (II)

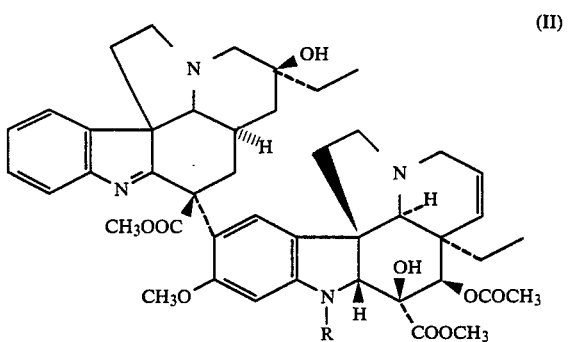

wherein R stands for methyl or formyl, as well as acid addition salts thereof which comprises oxidizing the vinblastine of formula (III)

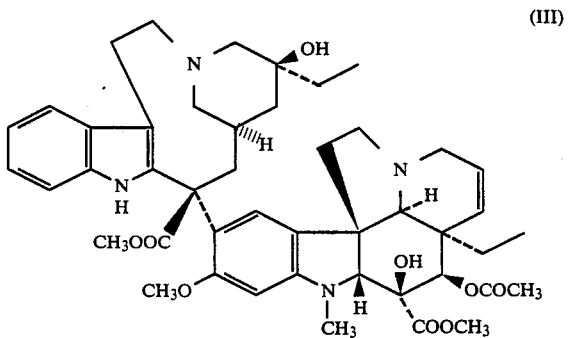

with chromium(VI) oxide or bichromate or chromic acid alcohol ester in an inert solvent, converting the compound of formula (II), wherein R stands for methyl, so obtained to the acid addition salt and optionally further oxidizing the acid addition salt obtained with an oxidizing agent as defined above and optionally converting the compound of formula (II), wherein R stands for formyl, so obtained to the acid addition salt.

According to a further feature of the invention there is provided a process for the preparation of vincristine of formula (I)

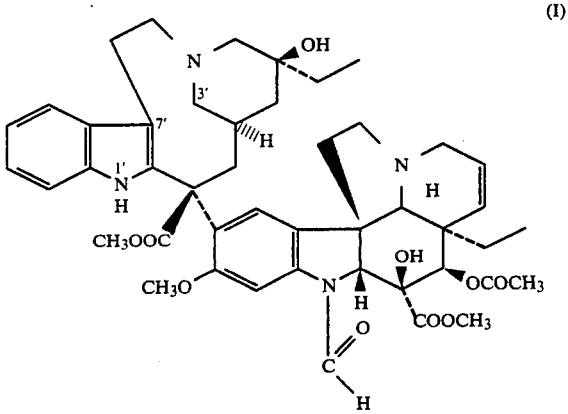

(I)

which comprises (a₁) oxidizing the compound of formula (II)

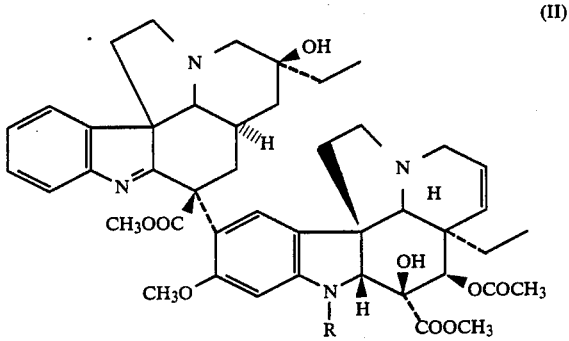

(II)

wherein R stands for methyl, or the acid addition salt thereof with chromium(VI) oxide or bichromate or chromic acid alcohol ester in an inert solvent and reducing the compound of formula (II), wherein R stands for formyl, so obtained with a borohydride and isolating the vincristine of formula (I) obtained, or (a₂) reducing the compound of formula (II)

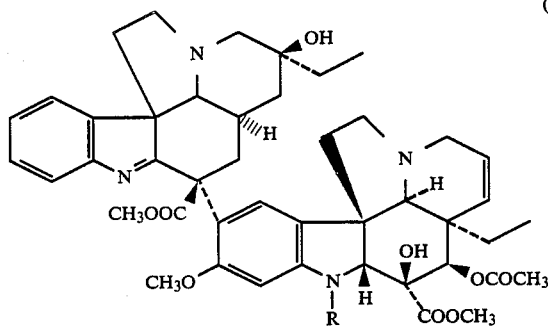

(II)

wherein R stands for formyl, with a borohydride and isolating the vincristine of formula (I) obtained.

According to the invention the new dimeric alkaloids of formula (II) are prepared from vinblastine of formula (III). The starting material is applied in form of the base.

The inert solvent used according to the invention is a solvent, which dissolves the starting material well. Preferably chlorinated hydrocarbons, mainly dichloromethane or chloroform, further ether solvents or the mixture thereof with chlorinated hydrocarbons are used. For promoting dissolution optionally aliphatic carboxylic acids having 2 to 10 carbon atoms, mainly acetic acid or propionic acid or weak aromatic acids, e.g. benzoic acid may be applied.

The vinblastine is oxidized in the above mentioned solvent or mixture of solvents. As oxidizing agent chromium(VI) oxide, bichromate or the ester of the chromium compound with an alkanol having 4 to 6 carbon atoms, preferably with tert.-butanol or tert.-amyl alcohol are used.

When chromium(VI) oxide is used as oxidizing agent, it is used in the presence of acetic anhydride and the oxidation is performed under $-10°$ C., preferably between $-30°$ C. and $-65°$ C.

When bichromate is used as oxidizing agent, it is applied in the presence of an acid and the oxidation is performed under $-10°$ C., preferably between $-30°$ C. and $-60°$ C.

When the ester of chromium(VI) oxide is used as oxidizing agent, which is preferably di(tert.-butyl)- or di(tert.-amyl)chromate, the reaction is carried out between $-10°$ C. and $+10°$ C.

After the oxidation reaction has been completed the pH of the reaction mixture is adjusted to 8 to 10 while taking care thereof that the temperature should not increase.

The product of the reaction is the cyclovinblastine which is isolated by extraction and evaporation and if necessary purified by column chromatography then converted to the acid addition salt, preferably sulfate salt (adding sulfuric acid in ethanol).

The cyclovinblastine salt may be converted to cyclovincristine by the oxidizing methods mentioned above. The reaction is completed in about 20 minutes. After completion of the reaction the pH is adjusted to 8 to 10 while taking care that the temperature of the reaction mixture should not increase, thereafter the reaction mixture is allowed to warm up to about 10° C. The product so obtained is isolated by extraction followed by evaporation and if necessary purified by column chromatography and if desired converted to the acid addition salt.

According to the invention the vincristine is prepared by the reduction of the cyclovincristine of formula (II). The reduction is performed with alkali metal borohydride, cyano borohydride or triacetoxy sodium borohydride in a suitable organic solvent, preferably in a lower aliphatic carboxylic acid. The reaction is performed at ambient temperature, the product obtained is isolated after eliminating the excess of the reducing agent by extraction and evaporation.

EXAMPLE 1

3',7'-Cyclovinblastine 0.50 g (0.6 mmole) of vinblastine base, which was set free freshly from its sulfate salt, is dissolved in the mixture of abs. dichloromethane (100 ml) and glacial acetic acid (12 ml). The solution obtained is cooled to $-55°$ C. and at this temperature the solution of 0.25 g (2.5 mmoles) chromium(VI) oxide in acetic anhydride (47 ml) cooled also to $-55°$ C. is added dropwise under vigorous stirring (within ca. 5 minutes) thereto. The reaction mixture is stirred at $-40°$ C. and the reaction is monitored by TLC (adsorbent: silica gel 60F₂₅₄, eluent: CH₂Cl₂/MeOH=20:2, $R_f$ of product > $R_f$ starting material). When the reaction has been completed (ca. 2 to 6 hours) the mixture of 100 ml concentrated aqueous ammonium hydroxide and 100 g ice is added to the solution and the reaction mixture obtained is stirred under external cooling for 10 minutes and at ambient temperature for further 10 minutes so that the acetic anhydride should be decomposed. After separating the phases the aqueous layer is extracted with dichloromethane (2×20 ml), the combined organic phase is washed with 2×30 ml of aqueous ammonia solution, then 2×20 ml of water and after drying evaporated in vacuo. So 0.45 g of the crude product is obtained which is purified by column chromatography (adsorbent: silica gel 0.04 to 0.063 mm, diameter of the column 15 mm, length of the column 200 mm, in dichloromethane, developing with dichloromethane containing 0.5% methanol, elution with dichloromethane containing 1% methanol).

Yield: 0.12 g (24%) 3',7'-cyclovinblastine.

IR (KBr): 740, 1030, 1210-1250, 1370, 1430, 1460, 1500, 1620, 1740, 2900, 3400 cm$^{-1}$,

MS (m/e): 822 (M+14), 808 (M, 100), 777, 749, 661, 650, 649, 648, 647, 541, 540, 524, 379, 353, 352, 309, 308, 283, 282, 281, 272, 268, 154, 144, 140, 135, 122, 121, 107, 93, 44, $^1$H—NMR (CDCl$_3$, 100 MHz): δ 0.42, 0.95 (2×t, 6, CH$_3$), 2.05 (s, 3, OCOCH$_3$), 2.72 (s, 3, N—CH$_3$), 3.68, 3.78 (3×t, 9, CO$_2$CH$_3$, OCH$_3$), 5.2 (d, 1, C$_{15}$H), 5.5 (s, 1, C$_{17}$H), 5.88 (dd, 1, C$_{14}$H), 6.15 (s, 1, C$_{12}$H), 6.88 (s, 1, C$_9$H), 7.1-7.5 (m, 4, C$_9$, —C$_{12}$, H), $^{13}$C—NMR (CDCl$_3$): δ 7.27, 7.66, 21.04, 30.93, 32.24, 32.77, 36.74, 37.34, 38.49, 39.65, 42.95, 43.75, 51.22, 52.19, 52.46, 53.13, 55.97, 56.13, 61.04, 63.54, 67.40, 71.05, 71.59, 76.58, 79.60, 83.57, 94.58, 120.76, 120.93, 121.37, 123.16, 123.88, 125.82, 127.53, 130.70, 147.81, 152.29, 153.61, 158.81, 170.74, 172.01, 174.24, 183.64.

EXAMPLE 2

3',7'-Cyclovincristine

The solution of 80 mg cyclovinblastine in abs. methanol (1 ml) is acidified with 1% solution of sulfuric acid in ethanol to pH=4, the sulfate salt is precipitated by the addition of abs. ether and dried in vacuo to yield 80 mg of alcohol-free cyclovinblastine sulfate (m.p. 255°-260° C., amorphous).

80 mg (0.09 mole) of the sulfate salt so obtained is dissolved in the mixture of abs. dichloromethane (20 ml) and glacial acetic acid (2 ml). The solution is cooled to −55° C. and at this temperature 40 mg of chromium(VI) oxide dissolved in 3.2 ml of acetic anhydride are added thereto. The reaction mixture is stirred at this temperature for 20 minutes. The pH of the reaction mixture is adjusted with the mixture of concentrated aqueous ammonia solution and 16 g ice to 9 at −50° C., thereafter the reaction mixture is allowed to warm up to +10° C. After separating the phases the aqueous layer is extracted with dichloromethane (3×15 ml), the combined organic phase is washed with 2×10 ml of a 1:1 mixture of concentrated aqueous solution and water, then with water (20 ml). After drying the solution obtained is evaporated in vacuo. So 67 mg of the crude product are obtained. The product obtained is purified by prepartive layer chromatography (mixture of ether/benzene/ethanol/diethylamine 100:5:5:5). The cyclovincristine is isolated from the zone having lower R$_f$-value.

Yield: 21 mg (29%).

M.p. 214°-219° C. (amorphous) C$_{46}$H$_{54}$N$_4$O$_{10}$ (822), [α]$_D$=−133° (c=1, CHCl$_3$), [α]$_{546}$=−166° (c=1, CHCl$_3$), IR (KBr): 760, 1030, 1200-1250, 1320, 1370, 1430, 1460, 1500, 1600, 1610, 1660, 1740, 2800, 3400-3450 cm$^{-1}$, $^1$H-NMR (CDCl$_3$, 100 MHz): δ 0.5, 0.9 (2×t, 6, CH$_3$), 2.0 (s, 1, OCOCH$_3$), 3.67, 3.73, 3.85 (3×s, 9, CO$_2$CH$_3$, OCH$_3$), 4.70 (m, 1, C$_2$H), 5.15 (s, 1, C$_{17}$H), 5.35 (d, 1, C$_{15}$H), 5.90 (dd, 1, C$_{14}$H), 6.55 (s, 1, C$_9$— or C$_{12}$H), 7.4-7.1 (m, 4, C$_9$, —C$_{11}$, H and C$_9$— or C$_{12}$H), 7.50 (m, 1, C$_{12}$, H), 8.0 and 8.75 (b, s, 1, N-CHO), $^{13}$C—NMR (CDCl$_3$): δ 7.25, 7.55, 20.94, 30.06, 32.20, 32.79, 36.69, 37.33, 39.69, 40.90, 42.38, 49.97, 50.34, 52.68, 52.84, 52.96, 53.10, 56.16, 56.39, 60.96, 63.68, 65.63, 71.03, 71.49, 71.53, 72.38, 75.87, 76.74, 77.14, 78.42, 79.78, 95.56, 120.77, 121.15, 122.50, 122.55 123.69, 124.22, 126.08, 127.67, 130.15, 130.34, 140.59, 147.83, 153.40, 158.66, 160.47, 160.51, 160.60, 170.06, 170.45, 170.53, 173.43, 182.73, MS (m/e): 836 (M+14), 823, 822 (M), 805, 792, 791 (100), 789, 764, 763, 673, 664, 663, 662, 605, 603, 583, 555, 554, 551, 393, 352, 315.5, 315, 154, 144, 140, 136, 135, 124, 122, 121, 44.

Alternatively 3',7'-cyclovincristine was prepared also from vincristine, the product obtained showed the same characteristics as the product prepared as described above.

The preparation was performed as follows:

450 mg (0.54 mmole) of vincristine base, which was set free from its sulfate salt, are dissolved in the mixture of abs. dichloromethane (100 ml), glacial acetic acid (25 ml) and methanol (1 ml). The solution obtained is cooled to −50° C. and at this temperature the solution of 0.25 g (2.5 mmoles) chromium(VI) oxide in 30 ml acetic anhydride cooled also to −50° C. is added dropwise within ca. 5 minutes. The oxidation reaction is monitored by TLC (adsorbent: Merck Kieselgel 60F$_{254}$; eluent: CH$_2$Cl$_2$/MeOH=20:2, R$_f$ of product>R$_f$ of starting material). After the addition of the oxidizing agent has been finished the reaction mixture is allowed to warm up to −20° C. and is kept at this temperature till the TLC spot of the starting material disappears (ca. 5 to 7 hours). When the reaction has been completed the mixture of 70 ml concentrated aqueous ammonium hydroxide solution and 70 g ice is poured to the solution cooled back to −50° C. The reaction mixture obtained is stirred at this temperature for 10 minutes and at ambient temperature for ca. 10 minutes so that the acetic anhydride should be decomposed. After separating the phases the aqueous solution is extracted with dichloromethane (3×20 ml), the combined organic phase (1:1) is washed with a 1:1 mixture of concentrated aqueous ammonium hydroxide solution and water (2×25 ml), then with water (2×20 ml), dried (MgSO$_4$) and evaporated in vacuo. The crude product obtained is purified by column chromatography (adsorbent: silicagel 0.063-0.2 mm; diameter of the column 20 mm, length of the column 150 mm, in dichloromethane; developing with dichloromethane containing 5% methanol; elution: with dichloromethane containing 1% methanol, then with dichloromethane containing 3% methanol).

Yield: 0.24 g (53%) 3',7'-cyclovincristine.

EXAMPLE 3

Vincristine

To the solution of 53 mg (0.06 mmole) cyclovincristine in 5 ml abs. glacial acetic acid an excess of sodium borohydride (ca. 40 mg) is added in portions at ambient temperature. The reaction is controlled by TLC (Merck Kieselgel 60F$_{254}$, R$_f$ of starting material>R$_f$ of product). When the reaction has been completed (ca. 2-3 hours at 25° C.), the solution is poured onto ice-water, rendered alkaline with concentrated aqueous ammonium hydroxide solution to pH 9, then extracted with 2×20 ml of dichloromethane. The combined organic phase is washed with 2×15 ml of water, dried (MgSO$_4$) and evaporated in vacuo. The crude product obtained is purified by preparative chromatography (Kieselgel PF$_{254+366}$).

Yield: 40 mg (75%) vincristine.

M.p. 220°-223° C. (amorphous). All the characteristic of the product obtained are the same as that of the natural substance.

IR (KBr): 720, 1020, 1120, 1200-1240, 1330, 1360, 1450, 1500, 1610, 1670, 1730, 2900, 3400 cm$^{-1}$, $^1$H—NMR (CDCl$_3$, 100 MHz): δ 0.89 (m, 6, CH$_3$), 2.07 (s, 3, OCOCH$_3$), 3.67, 3.72, 3.88 (3×s, 9, CO$_2$CH$_3$, OCH$_3$), 4.52, 4.74 (2×s, 1, C$_2$H), 5.25 (s, 1, C$_{17}$H), 5.40 (d, 1, C$_{15}$H), 5.92 (dd, 1, C$_{14}$H), 6.80, 6.93 (2×s, 2, C$_9$— and C$_{12}$H), 7.1-7.25 (m, 3, C$_9$, —C$_{11}$, H), 7.54 (m, 1, C$_{12}$, H), 8.06 (s, 1, NH), 8.17 and 8.76 (2×s, 1, >N—CHO), 9.4 (b, m, 1, OH).

What is claimed is:

1. A process for the preparation of vincristine of formula (I)

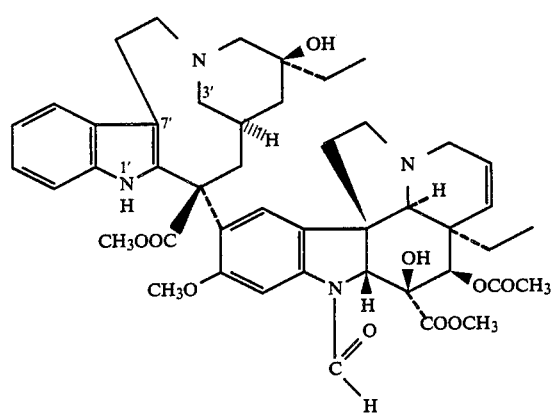

which comprises (a$_1$) oxidizing the compound of formula (II)

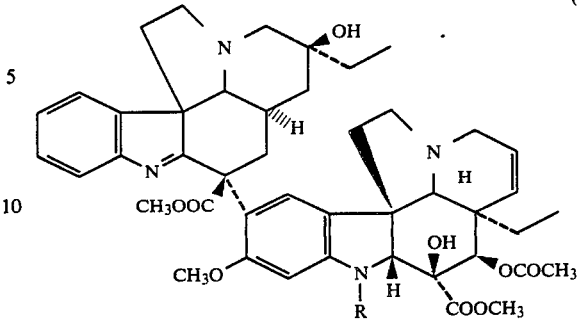

wherein R stands for methyl, or the acid addition salt thereof with chromium(VI) oxide or bichromate or chromic acid alcohol ester in an inert solvent to form the compound of the Formula (II) where R is formyl and selectively reducing the compound of formula (II), wherein P stands for formyl, so obtained with a borohydride and isolating the vincristine of formula (I) obtained, or (a$_2$) selectively reducing the compound of formula (II)

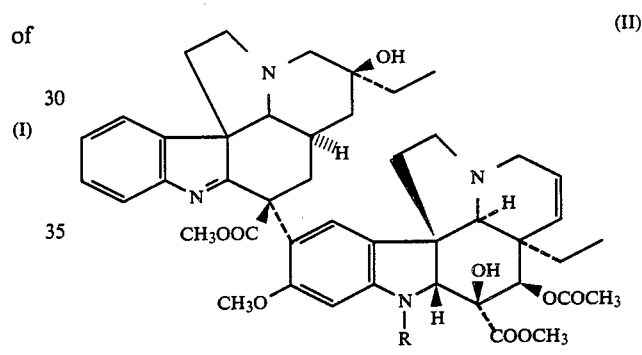

wherein R stands for formyl and isolating the vincristine of formula (I) obtained.

2. The process according to claim 1, variants (a$_1$) or (a$_2$), which comprises performing the selective reduction with a borohydride in an alkane carboxylic acid.

3. The process according to claim 1, variants (a$_1$) or (a$_2$), which comprises performing the selective reduction at ambient temperature.

* * * * *